(12) United States Patent
Ward et al.

(10) Patent No.: US 11,141,527 B2
(45) Date of Patent: Oct. 12, 2021

(54) CARTRIDGE FOR TUBING PLACEMENT IN A PERISTALTIC INFUSION PUMP

(71) Applicant: CME America, LLC, Golden, CO (US)

(72) Inventors: Brian William Ward, Littleton, CO (US); Lee William Travis, Centennial, CO (US)

(73) Assignee: CME AMERICA, LLC, Golden, CO (US)

( * ) Notice: Subject to any disclaimer, the term of this patent is extended or adjusted under 35 U.S.C. 154(b) by 57 days.

(21) Appl. No.: 16/175,799

(22) Filed: Oct. 30, 2018

(65) Prior Publication Data

US 2019/0125961 A1    May 2, 2019

Related U.S. Application Data

(60) Provisional application No. 62/579,542, filed on Oct. 31, 2017.

(51) Int. Cl.
*A61M 5/142* (2006.01)

(52) U.S. Cl.
CPC .... *A61M 5/14232* (2013.01); *A61M 5/14228* (2013.01); *A61M 2205/12* (2013.01); *A61M 2205/121* (2013.01); *A61M 2205/3334* (2013.01); *A61M 2207/00* (2013.01)

(58) Field of Classification Search
CPC .................. A61M 2205/12; A61M 2205/121
See application file for complete search history.

(56) References Cited

U.S. PATENT DOCUMENTS

| | | | |
|---|---|---|---|
| 5,397,222 A * | 3/1995 | Moss ................... | A61M 5/1413 417/477.2 |
| 5,482,446 A | 1/1996 | Williamson et al. | |
| 5,772,409 A | 6/1998 | Johnson | |
| 5,954,485 A * | 9/1999 | Johnson ............ | A61M 5/16831 417/474 |
| 2012/0191059 A1* | 7/2012 | Cummings ....... | A61M 5/14232 604/500 |
| 2014/0378901 A1 | 12/2014 | Rotem et al. | |

OTHER PUBLICATIONS

International Search Report and Written Opinion for Application No. PCT/US2018/058251, dated Feb. 4, 2019, 12 pages.

* cited by examiner

*Primary Examiner* — Emily L Schmidt
(74) *Attorney, Agent, or Firm* — Morgan, Lewis & Bockius LLP

(57) ABSTRACT

Removable tubing cartridges are described herein. A removable tubing cartridge includes an elongated cartridge body. The cartridge body further includes an upper lip disposed about the upper end of the cartridge body, wherein the upper lip extends axially away from the cartridge body. The cartridge can further include at least one lower fastener disposed about the lower end of the cartridge body, wherein the upper lip and the at least one lower fastener are configured to cooperatively align the cartridge body within the infusion pump. The cartridge can further include an upper tubing adapter cavity and a lower tubing adapter cavity that are configured to cooperatively align the pump segment tubing relative to the cartridge body.

18 Claims, 14 Drawing Sheets

CARTRIDGE FOR TUBING PLACEMENT IN A PERISTALTIC INFUSION PUMP

CROSS REFERENCE

This application claims priority from Provisional U.S. Application Ser. No. 62/579,542 filed on Oct. 31, 2017, and entitled CARTRIDGE FOR TUBING PLACEMENT IN A PERISTALTIC INFUSION PUMP.

FIELD OF THE INVENTION

The present disclosure generally relates to peristaltic infusion pumps, and, in particular, to removable cartridges for use with peristaltic infusion pumps.

BACKGROUND

Medical treatments often include dispensing precisely-metered quantities of a medical fluid (e.g. pain medications) to patients via a tubing set leading to an infusion site. Certain medical treatments may utilize a peristaltic infusion pump to dispense medication to the patient. Peristaltic infusion pumps may squeeze flexible tubing to provide positive fluid flow to the infusion site.

In some applications, during the setup and use of peristaltic infusion pumps, accurately and easily locating the flexible tubing within the peristaltic infusion pump may be difficult.

SUMMARY

The disclosed subject matter relates to removable cartridges for use with peristaltic infusion pumps. In certain embodiments, a removable tubing cartridge for aligning a pump segment tubing within an infusion pump is disclosed that comprises an elongated cartridge body comprising an upper end and a lower end; an upper lip disposed about the upper end of the cartridge body, wherein the upper lip extends axially away from the cartridge body in a first direction; at least one lower fastener disposed about the lower end of the cartridge body, wherein the at least one lower fastener extends axially away from the cartridge body in the first direction and the upper lip and the at least one lower fastener are configured to cooperatively align the cartridge body within the infusion pump; an upper tubing adapter cavity formed in the upper lip; and a lower tubing adapter cavity formed in the cartridge body, wherein the lower tubing adapter cavity is longitudinally spaced apart from the upper tubing adapter cavity and the upper tubing adapter cavity and the lower tubing adapter cavity are configured to cooperatively align the pump segment tubing relative to the cartridge body.

In certain embodiments, a removable tubing cartridge assembly for use with an infusion pump is disclosed that comprises an elongated cartridge body comprising an upper end and a lower end; an upper lip disposed about the upper end of the cartridge body, wherein the upper lip extends axially away from the cartridge body in a first direction; an upper tubing adapter cavity formed in the upper lip; a lower tubing adapter cavity formed in the cartridge body; a pump segment tubing comprising a first end and a second end, wherein the pump segment tubing extends from about the upper tubing adapter cavity to about the lower tubing adapter cavity; an upper tubing adapter coupled to the first end of the pump segment tubing, wherein the upper tubing adapter is configured to engage with the upper tubing adapter cavity; and a lower tubing adapter coupled to the second end of the pump segment tubing, wherein the lower tubing adapter is configured to engaged with the lower tubing adapter cavity, aligning the pump segment tubing longitudinally from the upper tubing adapter cavity to the lower tubing adapter cavity.

In certain embodiments, a method to install a removable tubing cartridge within an infusion pump is disclosed that comprises introducing an upper end of the cartridge to the infusion pump; engaging an upper lip of the cartridge with the infusion pump; introducing a lower end of the cartridge to the infusion pump; and engaging at least one lower fastener of the cartridge with the infusion pump.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The disclosed removable tubing cartridge incorporates features to align and support pump segment tubing within an infusion pump. The removable tubing cartridge can engage with portions of the pump segment tubing to align and support the tubing and can further include features to easily install the cartridge within the infusion pump.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to the administration of medical fluid to a patient by a medical practitioner using the disclosed removable tubing cartridge, it is to be understood that this description is only an example of usage and does not limit the scope of the claims. Various aspects of the disclosed removable tubing cartridges may be used in any application where it is desirable to position tubing with accuracy and ease.

Figure 1:
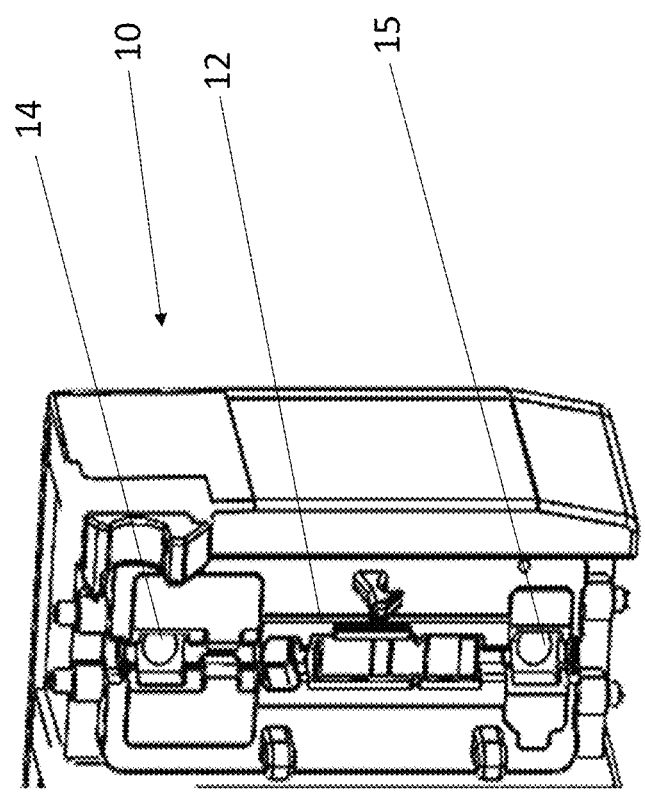
FIG. 1 is perspective view of an infusion pump, in accordance with various aspects of the present disclosure.

FIG. 1 is perspective view of an infusion pump 10, in accordance with various aspects of the present disclosure. In the depicted example, infusion pumps 10, such as peristaltic infusion pumps, are used to dispense precisely metered quantities of medication via a tubing set. During operation, the infusion pump 10 can pump fluid from a fluid reservoir to a patient.

As illustrated, the infusion pump 10 can include a recess 12 that can house a rolling mandrel and/or rollers to pump fluid through a pumping segment of tubing. The recess 12 can be generally rectangular and extend vertically along the front face of the infusion pump 10. In some embodiments, the recess 12 can include sensors 14, 15 to monitor fluid flow through the tubing.

The disclosed removable tubing cartridge overcomes several challenges discovered with respect to the operation and setup of certain conventional infusion pumps. One challenge with certain conventional infusion pumps is that skilled manual manipulation of the pumping segment of the tubing is required to install the tubing within the infusion pump 10. Because significant skilled manipulation is required to setup the pumping segment of the tubing within the infusion pump 10, excessive setup time or setup errors may occur. Further, a healthcare provider may be required to use two hands to setup the infusion pump.

Therefore, in accordance with the present disclosure, it is advantageous to provide a tubing cartridge as described herein that eliminates or substantially reduces the amount of skilled manual manipulation required to setup the pumping segment of the tubing within the infusion pump. The disclosed tubing cartridge provides ergonomic touch points and alignment features to align the tubing with the rollers or other pumping features of the infusion pump without the need for skilled manual manipulation. Advantageously, the disclosed tubing cartridge allows for production workers to consistently and reliably place the flexible pumping segment in the correct orientation during the assembly process, thereby reducing assembly errors. Further, for healthcare workers, the disclosed tubing cartridge simplifies insertion of the cartridge into the infusion pump in the correct orientation, reducing the risk of setup errors and enabling one handed operation. Additionally, the disclosed tubing cartridge enables the cartridge to be reliably inserted into an infusion pump without the need for trained healthcare worker oversight.

An example of a tubing cartridge that eliminates or substantially skilled manual manipulation of the tubing within an infusion pump is now described.

Figure 2:
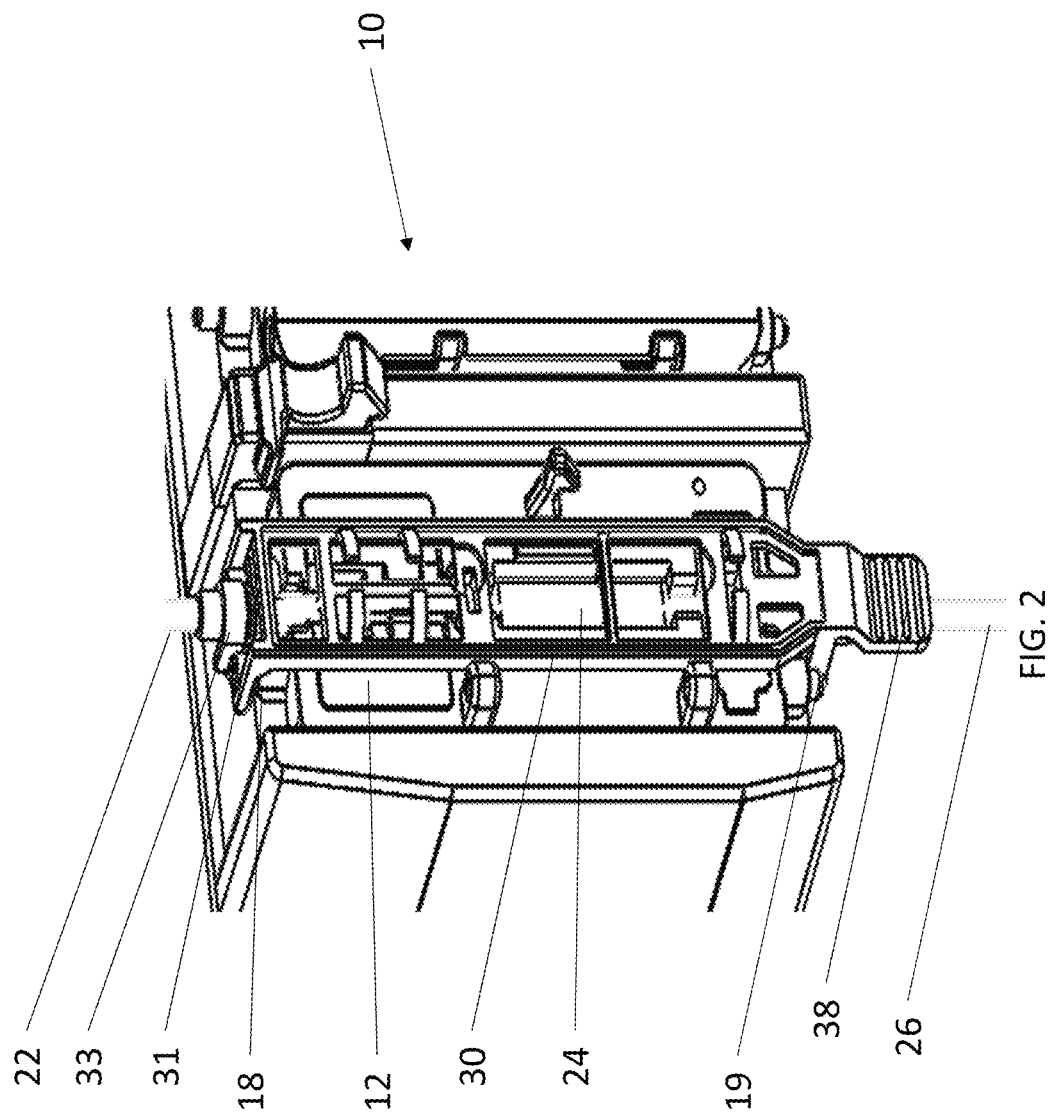
FIG. 2 is perspective view of an infusion pump with a cartridge installed, in accordance with various aspects of the present disclosure.

FIG. 2 is perspective view of an infusion pump 10 with a cartridge 30 installed, in accordance with various aspects of the present disclosure. In the illustrated embodiment, the infusion pump 10 pumps fluid to be administered from a fluid reservoir via an upstream semi-rigid tubing segment 22 to a patient via a downstream semi-rigid tubing segment 26.

In the depicted example, a section of pumping segment tubing 24 connects the upstream semi-rigid tubing segment 22 to the downstream semi-rigid tubing segment 26. Optionally, tubing adapters can connect the pumping segment tubing 24 to the upstream semi-rigid tubing segment 22 and the downstream semi-rigid tubing segment 26. During operation, the infusion pump 10 imparts a squeezing motion to the pumping segment tubing 24 to provide movement of the fluid within the pumping segment tubing 24 resulting in positive fluid flow from the reservoir, through the upstream semi-rigid tubing segment 22 to the downstream semi-rigid tubing segment 26 and to the infusion site.

In the depicted example, the infusion pump 10 can be a peristaltic pump. The infusion pump 10 can include a rotating mandrel and a plurality of rollers spaced around the peripheral of the mandrel. In some embodiments, the pumping segment tubing 24 can be flexible. During operation, the rollers of the infusion pump 10 can press against the pumping segment tubing 24 and squeeze the pumping segment tubing 24 flat between the rollers and any opposing features, such as features of the cartridge 30 as described herein to provide peristaltic movement of fluid within the pumping segment tubing 24.

Advantageously, the use of the cartridge 30 allows for the pumping segment tubing 24 to be aligned or otherwise engage with the rollers within the infusion pump 10 as they rotate around the pump mandrel. As illustrated, the pumping segment tubing 24 can be secured to the cartridge 30 to ensure proper alignment. The cartridge 30 further allows for the pumping segment tubing 24 to the releasably attached to the infusion pump 10.

By aligning the pumping segment tubing 24 within the infusion pump 10, the pumping segment tubing 24 can be aligned with the upstream and downstream optical sensors 14, 15 allowing for monitoring of fluid flow through the pumping segment tubing 24.

Further, in the depicted example, features of the cartridge 30 can allow for the cartridge 30 to be aligned and installed within the infusion pump 10, facilitating proper alignment of the pumping segment tubing 24 relative to the infusion pump 10. For example, features formed within the upper lip 31 extending from the cartridge 30 can engage the upper pins 18 of the infusion pump 10. Similarly, engagement features extending from the lower end of the cartridge 30 can engage the lower pins 19 of the infusion pump 10. The engagement features of the cartridge 30 can ensure that the cartridge 30 is aligned within the recess 12 and engaged with the infusion pump 10.

Figure 3:
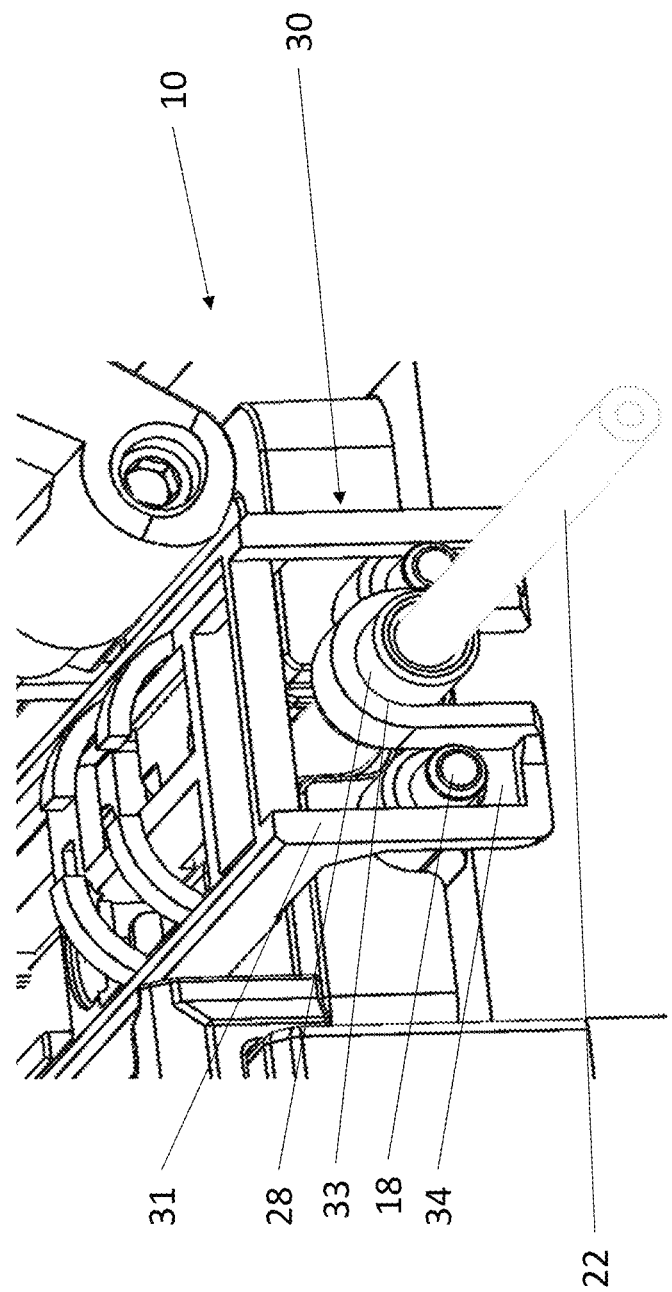
FIG. 3 is an upper detail perspective view of the infusion pump with the cartridge installed of FIG. 2, in accordance with various aspects of the present disclosure.
Figure 4:
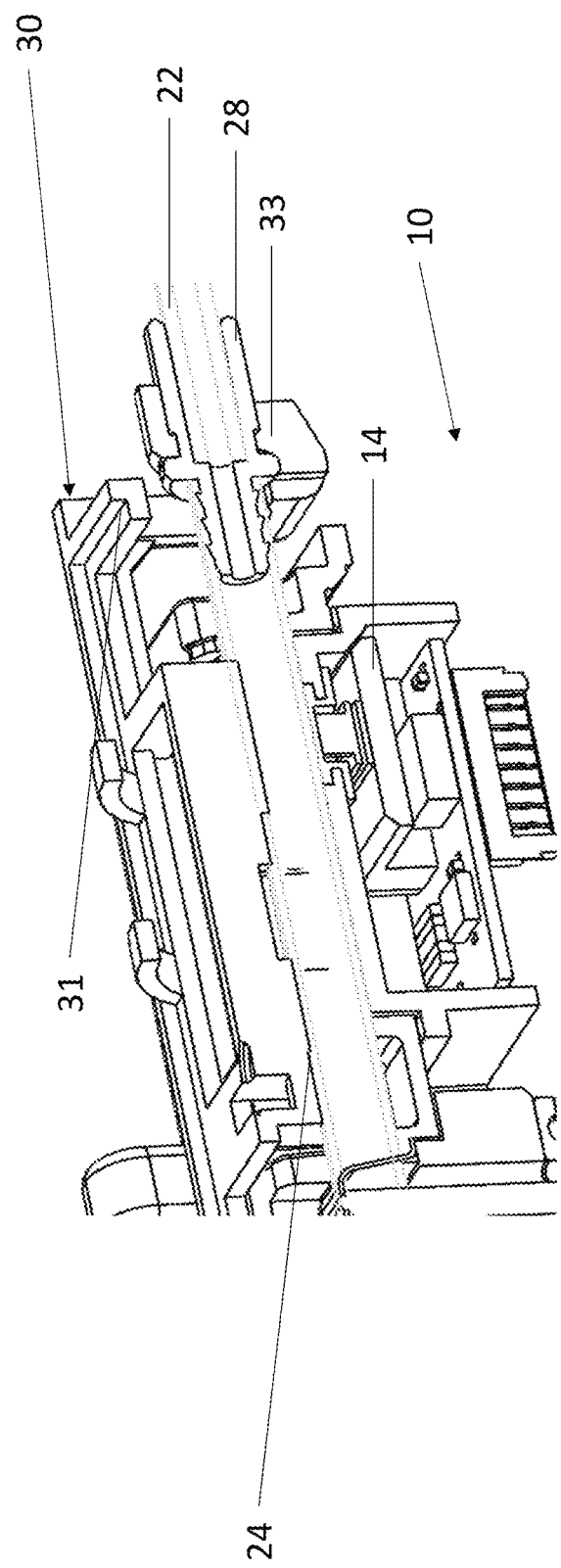
FIG. 4, is a partial upper cross-sectional view of the infusion pump with the cartridge installed of FIG. 2, in accordance with various aspects of the present disclosure.

FIG. 3 is an upper detail perspective view of the infusion pump 10 with the cartridge 30 installed of FIG. 2, in accordance with various aspects of the present disclosure. Further, FIG. 4 is a partial upper cross-sectional view of the infusion pump 10 with the cartridge 30 installed of FIG. 2, in accordance with various aspects of the present disclosure. With reference to FIGS. 3 and 4, the upper end of the cartridge 30 is shown. During operation, fluid from the reservoir is drawn through the upstream semi-rigid tubing segment 22 due to the pumping motion imparted on the pumping segment tubing 24. In some embodiments, the sensor 14 can monitor the fluid flow into the infusion pump 10.

In the depicted example, the upstream semi-rigid tubing segment 22 is coupled to the pumping segment tubing 24 with a tubing adapter 28. Optionally, the tubing adapter 28 can have a friction fit or an interference fit with the upstream semi-rigid tubing segment 22. In some embodiments, the tubing adapter 28 receives the outer diameter of the upstream semi-rigid tubing segment 22.

Similarly, the pumping segment tubing 24 can have a friction fit or interference fit with the tubing adapter 28. In some embodiments, the tubing adapter 28 utilizes a barb fitting to engage the pumping segment tubing 24. As illustrated, the tubing adapter 28 may engage the inner diameter of the pumping segment tubing 24.

In the depicted example, the tubing adapter 28 can have a generally circular outer profile or any other suitable profile. In some embodiments, the tubing adapter 28 is retained or engaged by the cartridge 30.

For example, an upper tubing adapter seat or cavity 33 can engage the outer profile of the tubing adapter 28 to retain the pumping segment tubing 24 relative to the cartridge 30. In some embodiments, the tubing adapter seat 33 can have a complimentary profile to the outer profile of the tubing adapter 28. For example, the tubing adapter seat 33 can have a generally semi-circular mating profile. In some embodiments, the mating profile can extend generally towards the cartridge body. The tubing adapter seat 33 can further have a spring bias to frictionally engage the tubing adapter 28.

In the depicted example, the tubing adapter seat 33 is formed in the upper lip 31 of the cartridge 30. The upper lip 31 can extend in an axial direction to extend into the recess 12 of the infusion pump 10.

As illustrated, the upper end of the cartridge 30 can be aligned with recess 12 and generally engaged with the infusion pump 10 to permit the pumping segment tubing 24 to be properly aligned within the infusion pump 10. For example, the upper lip 31 can include one or more installation hoops 34 formed therethrough. In some embodiments, the installation hoops 34 can engage or otherwise contact the upper pins 18 of the infusion pump 10 to locate or register the upper end of the cartridge 30 relative to the infusion pump 10. The installation hoops 34 can be formed in the space defined by the outer profile of the tubing adapter seat 33.

Figure 5:
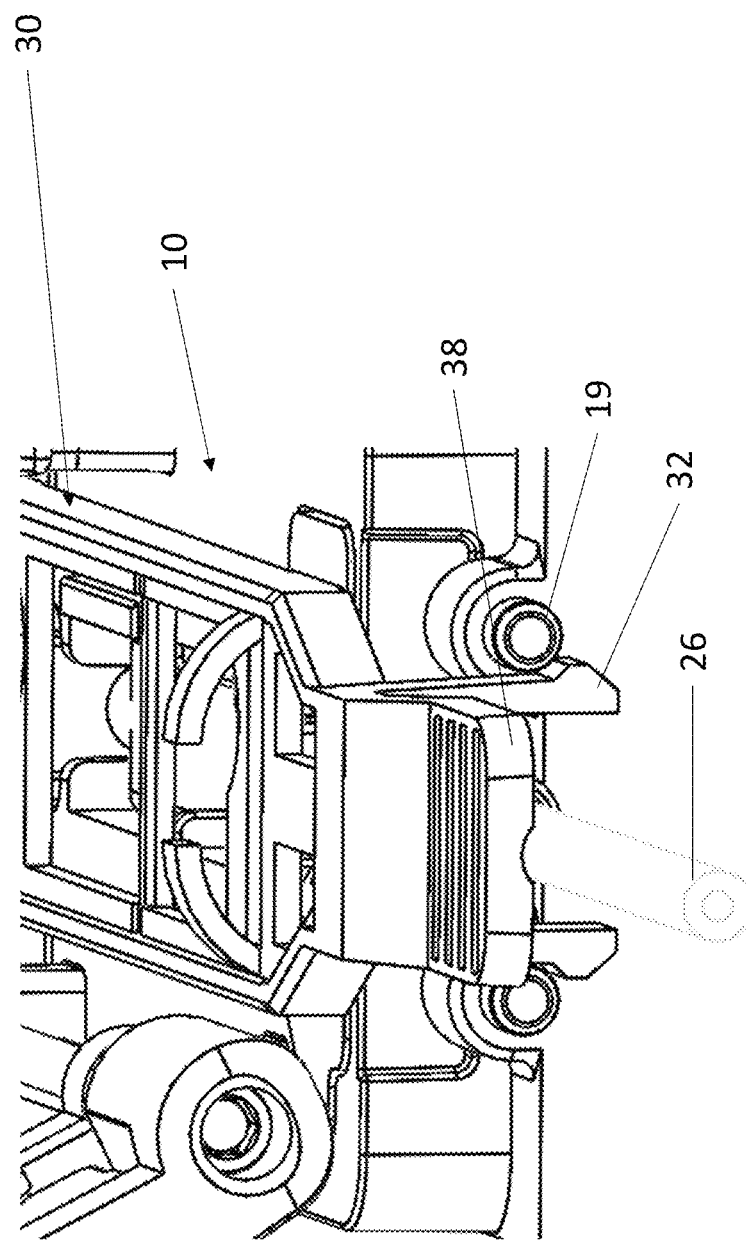
FIG. 5 is a lower detail perspective view of the infusion pump with the cartridge installed of FIG. 2, in accordance with various aspects of the present disclosure.
Figure 6:
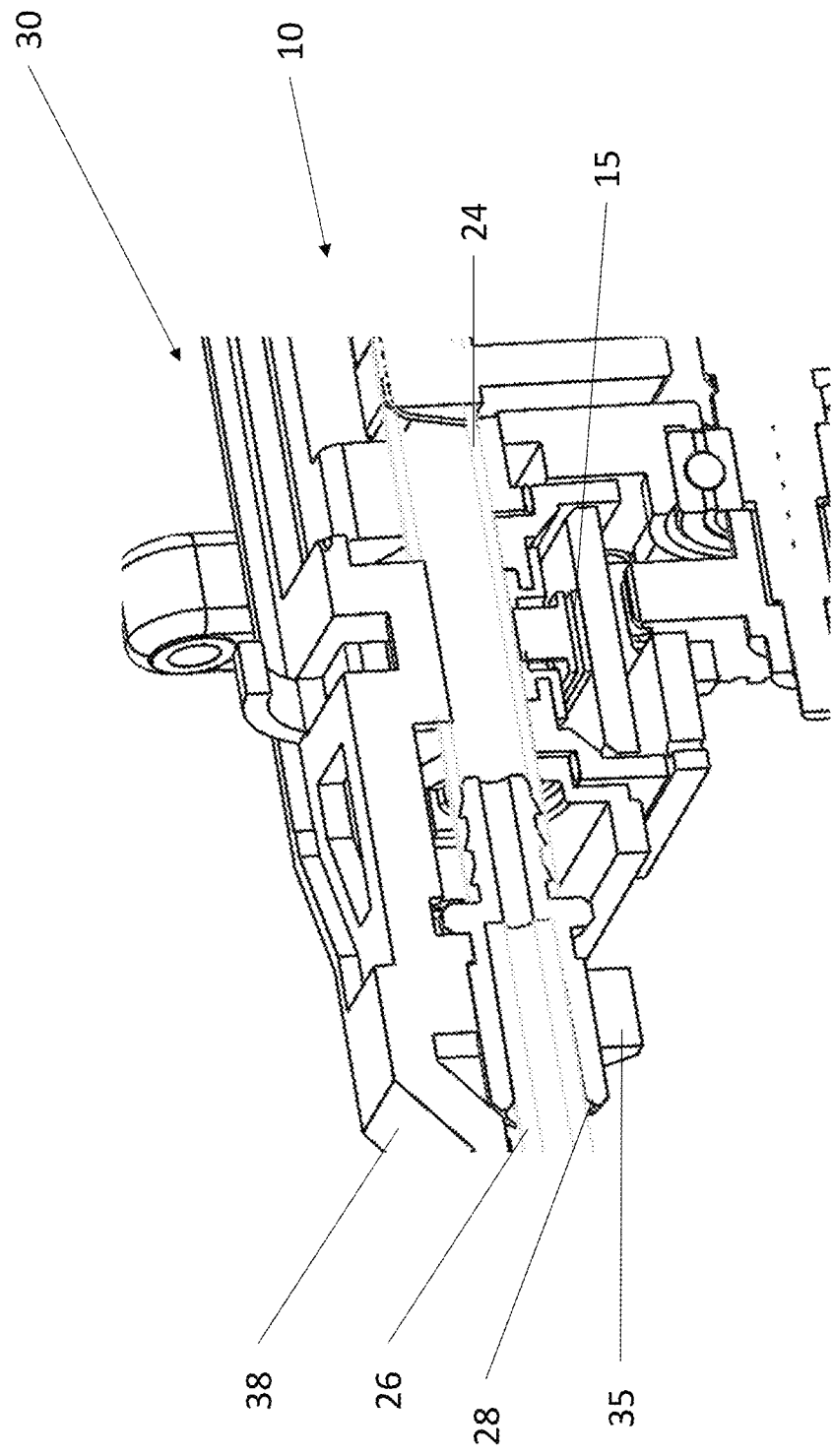
FIG. 6, is a partial lower cross-sectional view of the infusion pump with the cartridge installed of FIG. 2, in accordance with various aspects of the present disclosure.

FIG. 5 is lower detail perspective view of the infusion pump 10 with the cartridge 30 installed of FIG. 2, in accordance with various aspects of the present disclosure. Further, FIG. 6 is a partial lower cross-sectional view of the infusion pump 10 with the cartridge 30 installed of FIG. 2, in accordance with various aspects of the present disclosure. With reference to FIGS. 5 and 6, the lower end of the cartridge 30 is shown. During operation, fluid is pumped from the pumping segment tubing 24 to the infusion site through the downstream semi-rigid tubing segment 26. In some embodiments, the sensor 15 can monitor the fluid flow out of the infusion pump 10.

In the depicted example, the downstream semi-rigid tubing segment 26 is coupled to the pumping segment tubing 24 with a tubing adapter 28. Optionally, the tubing adapter 28 can have a friction fit or an interference fit with the downstream semi-rigid tubing segment 26. In some embodiments, the tubing adapter 28 receives the outer diameter of the downstream semi-rigid tubing segment 26.

Similarly, the pumping segment tubing 24 can have a friction fit or interference fit with the tubing adapter 28. In some embodiments, the tubing adapter 28 utilizes a barb fitting to engage the pumping segment tubing 24. As illustrated, the tubing adapter 28 may engage the inner diameter of the pumping segment tubing 24.

In the depicted example, the tubing adapter 28 can have a generally circular outer profile or any other suitable profile. In some embodiments, the tubing adapter 28 is retained or engaged by the cartridge 30.

For example, a lower tubing adapter seat or cavity 35 can engage the outer profile of the tubing adapter 28 to retain the pumping segment tubing 24 relative to the cartridge 30. In some embodiments, the tubing adapter seat 35 can have a complimentary profile to the outer profile of the tubing adapter 28. For example, the tubing adapter seat 35 can have a generally semi-circular mating profile. In some embodiments, the mating profile can extend generally towards the cartridge body. The tubing adapter seat 35 can further have a spring bias to frictionally engage the tubing adapter 28.

In the depicted example, the tubing adapter seat 35 is formed in a protrusion of the cartridge 30. The protrusion can extend in an axial direction to extend into the recess 12 of the infusion pump 10.

As illustrated, the lower end of the cartridge 30 can be aligned with recess 12 and generally engaged with the infusion pump 10 to permit the pumping segment tubing 24 to be properly aligned within the infusion pump 10. For example, a set of fasteners 32 can extend axially from the cartridge 30 toward the recess 12. In some embodiments, the fasteners 32 can engage or otherwise contact the lower pins 19 of the infusion pump to engage the lower end of the cartridge 30 relative to infusion pump. The fasteners 32 can be outwardly biased members to engage the inner surfaces of the lower pins 19. Optionally, the fasteners 32 can be disposed laterally adjacent to the tubing adapter seat 35.

In some embodiments, a finger tab 38 can be utilized to allow a user to ergonomically manipulate the cartridge 30. In the depicted example, the finger tab 38 is a generally planar surface that allows for the user to easily push or pull the cartridge 30 at the lower end of the cartridge 30. For example, the finger tab 38 can allow the user to easily engage or disengage the fasteners 32 with the lower pins 19 of the infusion pump 10. Optionally, the finger tab 38 can include a plurality of grooves.

Figure 7:
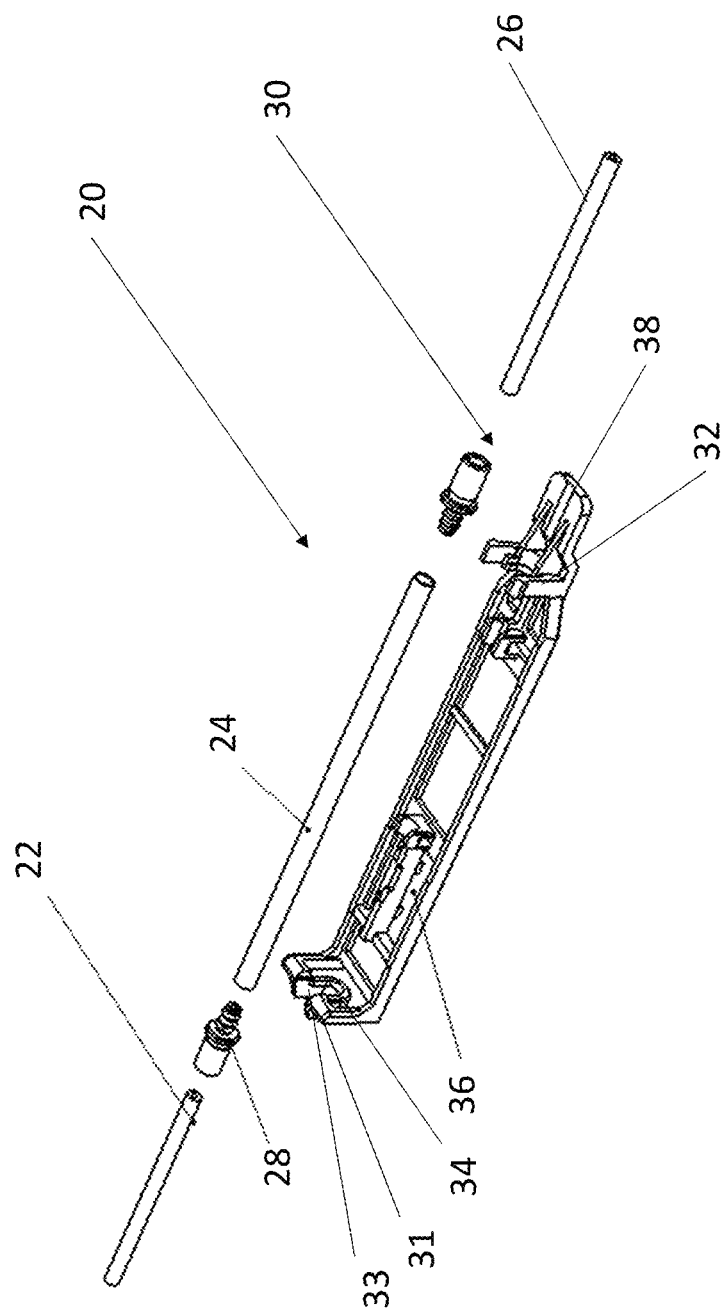
FIG. 7 is an exploded view of the cartridge of FIG. 2, in accordance with various aspects of the present disclosure.
Figure 8:
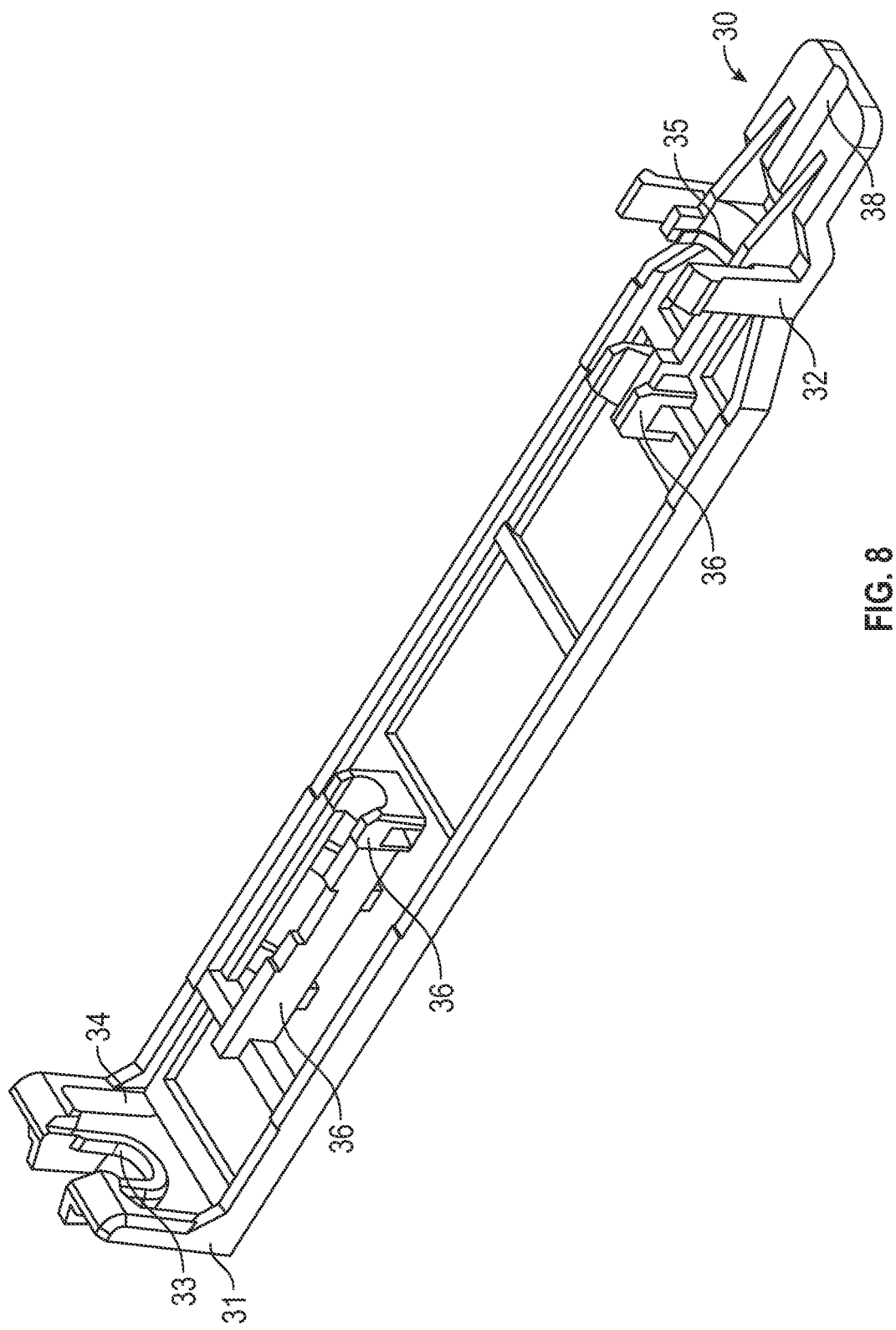
FIG. 8 is a perspective view of the cartridge, in accordance with various aspects of the present disclosure.

FIG. 7 is an exploded view of the cartridge 30 of FIG. 2, in accordance with various aspects of the present disclosure. Further, FIG. 8 is a perspective view of the cartridge 30, in accordance with various aspects of the present disclosure. With reference to FIGS. 7 and 8, the cartridge 30 configured to align and locate the pumping segment tubing 24 within the infusion pump 10 is shown.

In the depicted example, the cartridge 30 can be molded as a single piece of plastic or polymer. The cartridge 30 can generally have an elongated body configured for insertion into a corresponding channel or recess 12 of the infusion pump 10. Optionally, the cartridge 30 have a generally rectangular shape. As illustrated, the cartridge 30 can be generally configured to be disposed adjacent to the rollers within the recess 12.

As previously described, the cartridge 30 is configured to be used in conjunction with the tubing set 20 having an upstream semi-rigid tubing segment 22 leading from a reservoir, a short intermediate pumping segment tubing 24 made of flexible tubing, and downstream semi-rigid tubing segment 26 leading to the patient. All three tubing segments 22, 24 and 26 are connected in series by tubing adapters 28.

In the depicted example, the tubing adapter seats 33, 35 at either end of the cartridge 30 grip the tubing adapters 28 of the tubing set 20, aligning and extending the pumping segment tubing 24. Further, as the tubing adapter seats 33, 35 are longitudinally spaced a fixed distance apart, the tension on the pumping segment tubing 24 is controlled, preventing pulling or twisting of the pumping segment tubing 24. Advantageously, by controlling the tension on the pumping segment tubing 24, the pumping segment tubing 24 can be aligned with sensors 14, 15 mitigating undetected delivery errors.

Further, additional tubing location features 36 on the posterior aspect of the cartridge 30 hold the flexible pumping segment tubing 24 in alignment with the midline of the cartridge 30 along its length, so that the flexible pumping segment tubing 24 will be compressed by the pump rollers during operation of the infusion pump 10. Tubing location features 36 can be disposed about the upper and/or lower end of the cartridge 30. Optionally, these tubing location features 36 also maintain proper alignment of the flexible pumping segment tubing 24 is over two sensors 14, 15 housed in the recess 12 of the infusion pump 10 that monitor the fluid in the flexible pumping segment tubing 24 upstream and downstream from the pumping mechanism to detect occlusions and air bubbles in the flexible pumping segment tubing 24. In some embodiments, the tubing location features 36 can include protrusions or bosses configured to support the pumping segment tubing 24.

In addition to aligning the pumping segment tubing 24, the shape of the cartridge 30 can allow the cartridge 30 to register in a desired position and alignment with respect to the recess 12 of the infusion pump 10. In some embodiments, the upper lip 31 projects from the upper end of the cartridge 30 to form a generally L-shaped structure.

Figure 9:
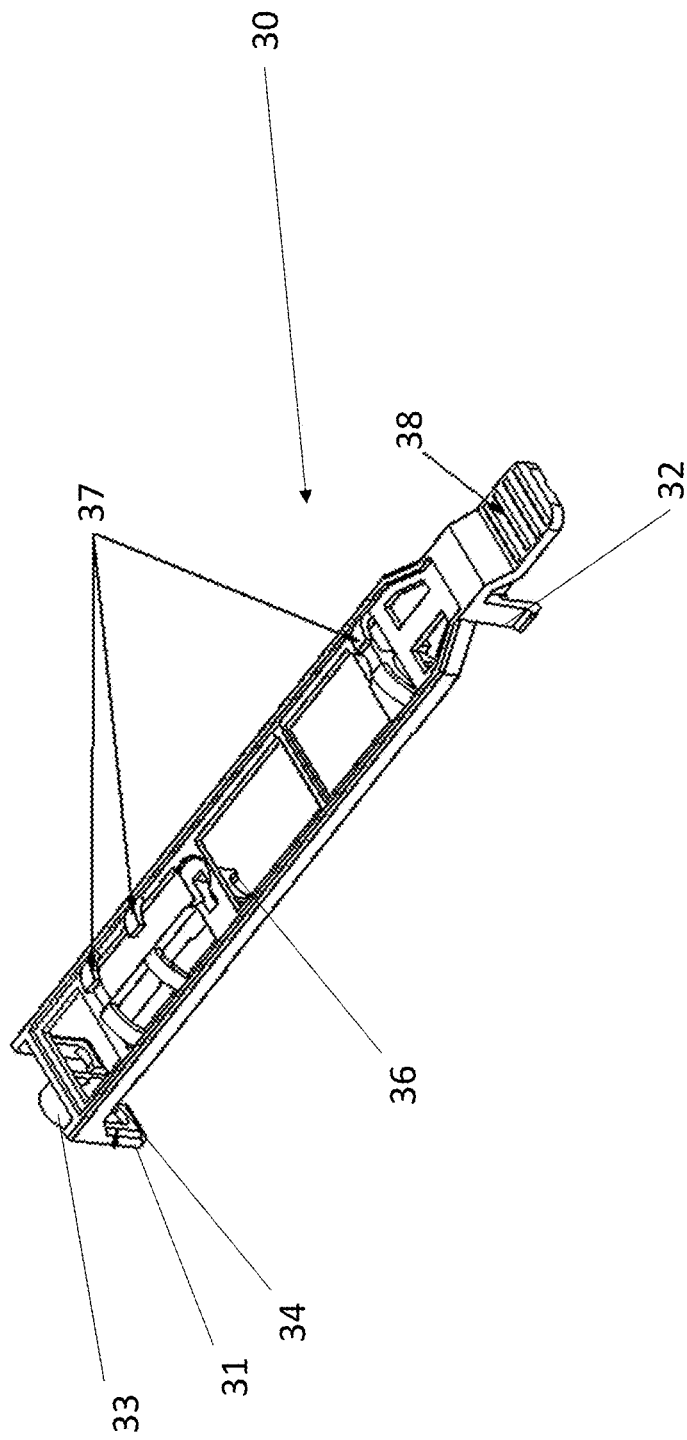
FIG. 9 is a perspective view of the cartridge, in accordance with various aspects of the present disclosure.

FIG. 9 is a perspective view of the cartridge, in accordance with various aspects of the present disclosure. In the depicted example, leaf springs 37 can be utilized to firmly engage the cartridge 30 against mating features of the infusion pump 10. Optionally, the leaf springs 37 can extend axially away from the cartridge 30 and the recess 12 of the infusion pump 10. The leaf springs 37 can axially bias the cartridge 30 toward the recess 12, increasing the accuracy in positioning the cartridge 30 with respect to the recess 12 and the pump sensors 14, 15 disposed within the recess 12.

Further, as previously described, the finger tab 38 can be utilized to manipulate the cartridge 30.

Figure 10:
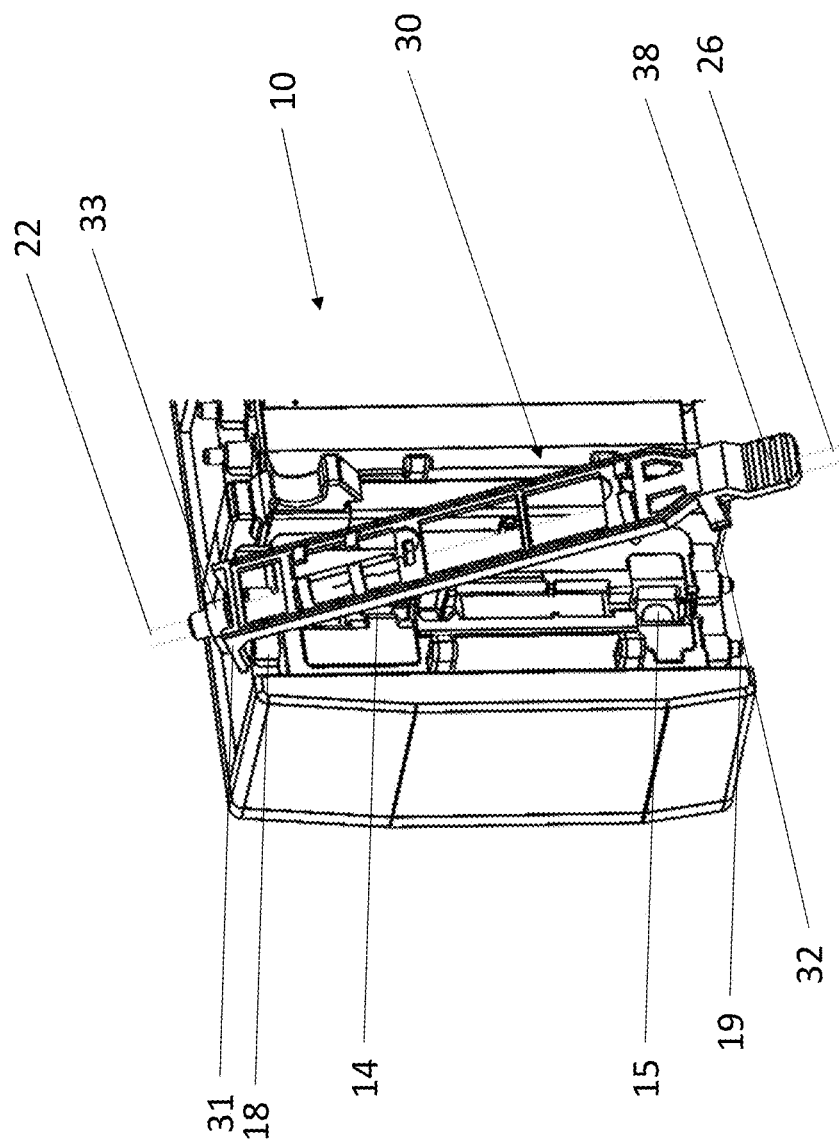
FIG. 10 is a perspective view of an infusion pump with a cartridge partially attached thereto, in accordance with various aspects of the present disclosure.

FIG. 10 is a perspective view of an infusion pump with a cartridge partially attached thereto, in accordance with various aspects of the present disclosure. FIG. 10 depicts the insertion of the cartridge 30 and tubing set 20 into the recess 12 in the front of the infusion pump 10. During installation, the upper end of the cartridge 30 is initially inserted into the recess 12 so that the upper lip 31 of the cartridge 30 engages upper registration features adjacent to the upper end of the recess 12 (e.g., two pins or bosses 18 extending upward adjacent to the upper edge of the recess 12). For example, the upper lip 31 can be equipped with installation hoops 34 (e.g., openings or recesses) to receive the upper pins 18 to allow the cartridge 30 to pivot about the upper pins 18.

Figure 11:
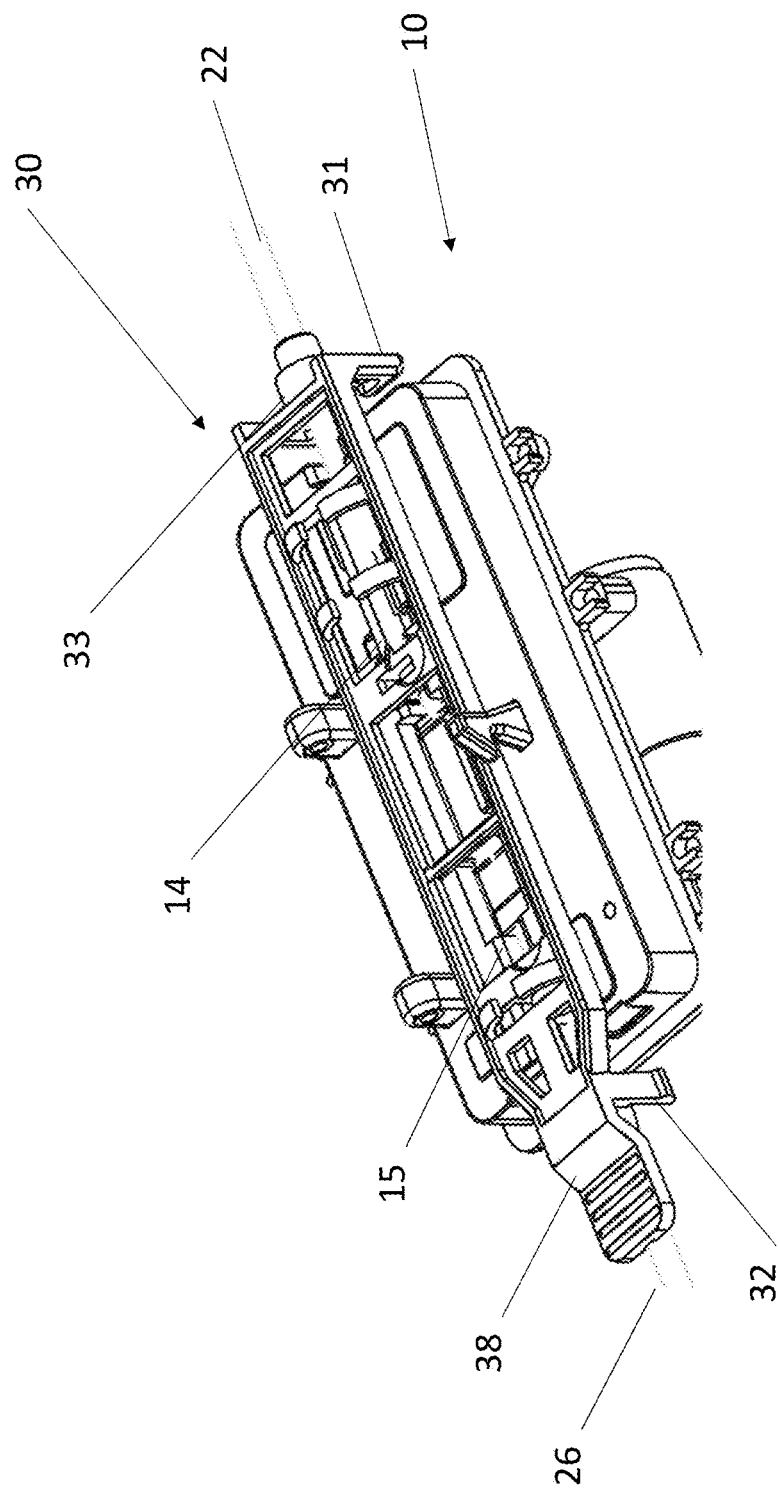
FIG. 11 is a perspective view of an infusion pump with a cartridge with various components removed, in accordance with various aspects of the present disclosure.
Figure 12:
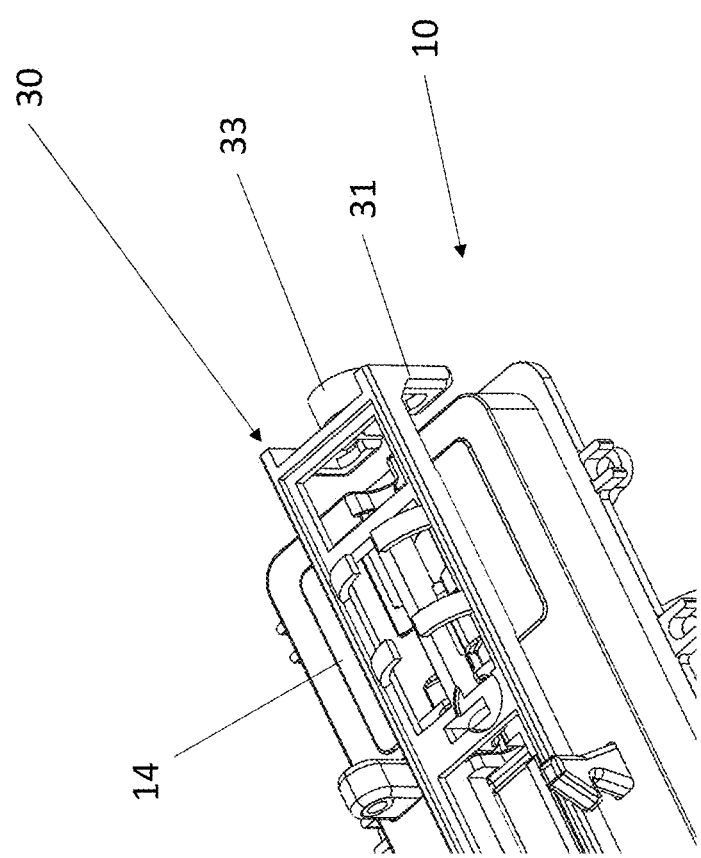
FIG. 12 is an upper detail perspective view of the infusion pump with the cartridge of FIG. 11, in accordance with various aspects of the present disclosure.

FIG. 11 is a perspective view of an infusion pump with a cartridge with various components removed, in accordance with various aspects of the present disclosure. Further, FIG. 12 is an upper detail perspective view of the infusion pump with the cartridge of FIG. 11, in accordance with various aspects of the present disclosure. With reference to FIGS. 11 and 12, after engaging the upper registration features, the cartridge 30 can be pivoted into the lower section of the recess 12, by pushing on the finger tab 38 protruding downward from the lower end of the cartridge 30. A set of fasteners 32 (e.g., snaps) on the lower posterior aspect of the cartridge 30 removably engage lower registration features (e.g., two pins 19 extending downward adjacent to the lower end of the recess 12) to hold the cartridge 30 and tubing set 20 in the recess 12. In the depicted example, the upper lip 31 of the cartridge 30 is in contact with the upper edge of the recess 12, and the main body of the cartridge 30 is held laterally between the side walls of the recess 12 to ensure accurate registration of the cartridge 30 in the recess 12. In turn, this ensures accurate registration of the flexible pumping segment tube 24 with respect to the pumping mechanism.

Figure 13:
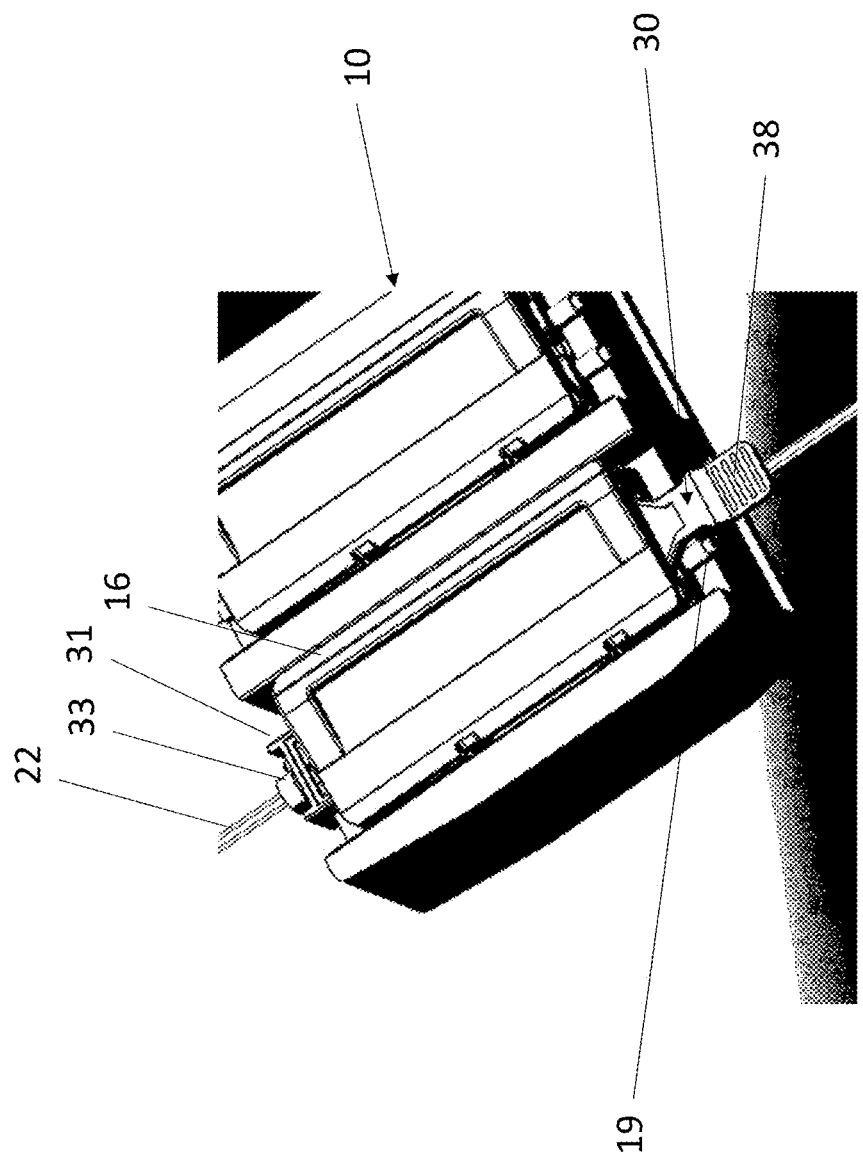
FIG. 13 is a perspective view of an infusion pump with a cover door, in accordance with various aspects of the present disclosure.
Figure 14:
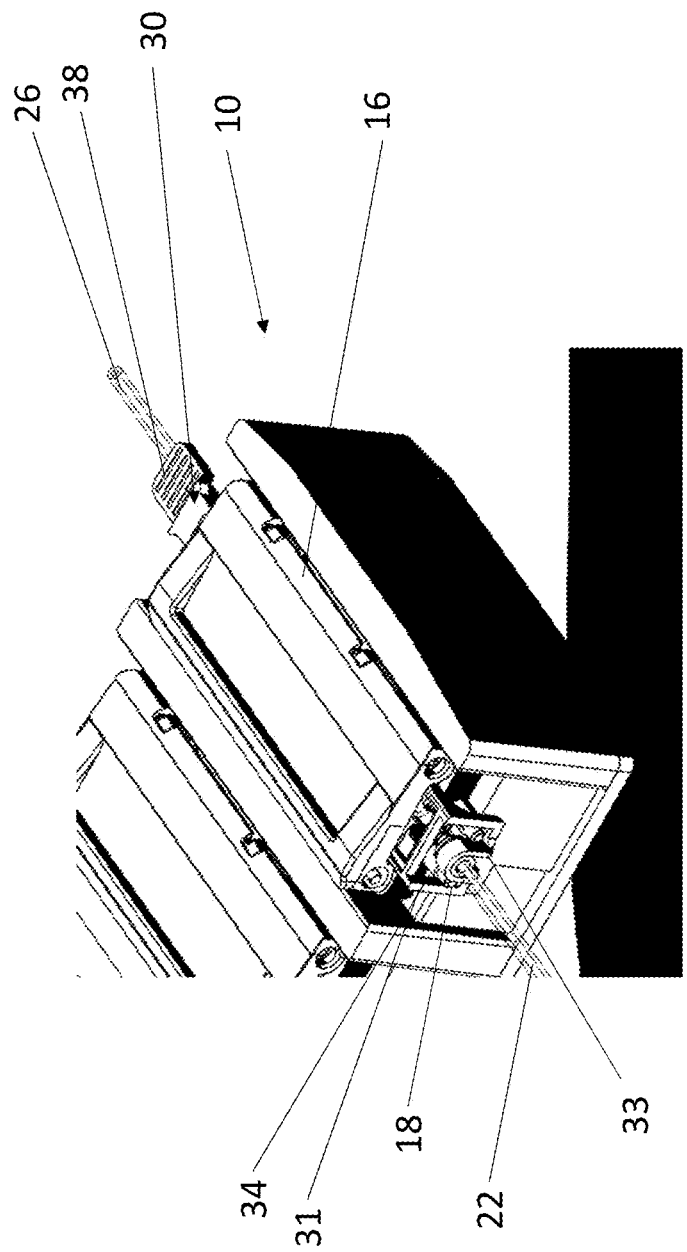
FIG. 14 is a perspective view of an infusion pump with a cover door of FIG. 13, in accordance with various aspects of the present disclosure.

FIG. 13 is a perspective view of an infusion pump with a cover door, in accordance with various aspects of the present disclosure. Further, FIG. 14 is a perspective view of an infusion pump with a cover door of FIG. 13, in accordance with various aspects of the present disclosure. With reference to FIGS. 13 and 14, optionally, the infusion pump 10 can be equipped with a cover door 16 to enclose the cartridge 30 within the recess 12. The cover door 16 may assist proper registration of the cartridge 30 and pumping segment tubing 24 with respect to the pumping mechanism of the infusion pump 10. As previously described, leaf springs 37 can urge against the cover door 16 to locate the cartridge 30 firmly against mating features of the pumping mechanism.

As needed, the cartridge 30 can be released by pivoting the cover door 16 to its open position. The user can then pull forward on the finger tab 38 to release the lower fasteners 32 from the lower pins 19. The lower end of the cartridge 30 can then be pivoted outward from the recess 12 in the infusion pump 10. Finally, the user lifts upward on the cartridge 30 to release the installation hoops 34 on the upper lip 31 of the cartridge 30 from the upper pins 18, and thereby releases the cartridge 30.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A removable tubing cartridge for aligning a pump segment tubing within an infusion pump, the cartridge comprising:
    an elongated cartridge body comprising an upper end and a lower end;
    an upper lip disposed about the upper end of the cartridge body, wherein the upper lip extends axially away from the cartridge body in a first direction;
    at least one lower fastener disposed about the lower end of the cartridge body,
    wherein the at least one lower fastener extends axially away from the cartridge body in the first direction and the upper lip and the at least one lower fastener are configured to cooperatively align the cartridge body within the infusion pump;
    an upper tubing adapter cavity formed in the upper lip, the upper tubing adapter cavity having a mating profile defining an opening of the upper tubing adapter cavity to receive an upper tubing adapter, wherein the mating profile defines a generally semi-circular mating profile extending from an edge of the upper lip, wherein the edge of the upper lip is configured to engage at least one upper pin of the infusion pump, and the semi-circular mating profile extends from the edge of the upper lip toward the cartridge body; and
    a lower tubing adapter cavity formed in the cartridge body, wherein the lower tubing adapter cavity is longitudinally spaced apart from the upper tubing adapter cavity and the upper tubing adapter cavity and the lower tubing adapter cavity are configured to cooperatively align the pump segment tubing relative to the cartridge body,
    wherein the upper lip has a spring bias to frictionally engage the upper tubing adapter within the mating profile.

2. The cartridge of claim 1, wherein the cartridge body comprises a polymer.

3. The cartridge of claim 1, wherein the cartridge body comprises a rectangular shape.

4. The cartridge of claim 1, further comprising at least one tubing locating feature extending axially away from the cartridge body in the first direction.

5. The cartridge of claim 4, wherein the at least one tubing locating feature comprises an upper tubing locating feature.

6. The cartridge of claim 4, wherein the at least one tubing locating feature comprises a lower tubing locating feature.

7. The cartridge of claim 1, wherein the at least one lower fastener comprises a laterally biased member.

8. The cartridge of claim 1, further comprising a tab portion adjacent to the at least one lower fastener.

9. The cartridge of claim 1, further comprising a plurality of axially biasing members extending axially away from the cartridge body in a second direction, wherein the second direction is opposite to the first direction.

10. The cartridge of claim 1, wherein the at least one lower fastener is disposed laterally adjacent to the lower tubing adapter.

11. The cartridge of claim 1, further comprising at least one installation hoop formed through the upper lip, wherein the at least one installation hoop is configured to align the cartridge body with the infusion pump.

12. A removable tubing cartridge assembly for use with an infusion pump, the cartridge assembly comprising:
- an elongated cartridge body comprising an upper end and a lower end;
- an upper lip disposed about the upper end of the cartridge body, wherein the upper lip extends axially away from the cartridge body in a first direction;
- an upper tubing adapter cavity formed in the upper lip, the upper tubing adapter cavity having a mating profile defining an opening of the upper tubing adapter cavity, wherein the mating profile defines a generally semi-circular mating profile extending from an edge of the upper lip, wherein the edge of the upper lip is configured to engage at least one upper pin of the infusion pump, and the semi-circular mating profile extends from the edge of the upper lip toward the cartridge body;
- a lower tubing adapter cavity formed in the cartridge body;
- a pump segment tubing comprising a first end and a second end, wherein the pump segment tubing extends from about the upper tubing adapter cavity to about the lower tubing adapter cavity;
- an upper tubing adapter coupled to the first end of the pump segment tubing, wherein the upper tubing adapter is configured to be inserted into the opening of the upper tubing adapter cavity and engage with the upper tubing adapter cavity; and
- a lower tubing adapter coupled to the second end of the pump segment tubing, wherein the lower tubing adapter is configured to engaged with the lower tubing adapter cavity, aligning the pump segment tubing longitudinally from the upper tubing adapter cavity to the lower tubing adapter cavity,
- wherein the upper lip has a spring bias to frictionally engage the upper tubing adapter within the mating profile.

13. The cartridge assembly of claim 12, further comprising at least one lower fastener disposed about the lower end of the cartridge body, wherein the at least one lower fastener extends axially away from the cartridge body in the first direction and the upper lip and the at least one lower fastener are configured to cooperatively align the cartridge body within the infusion pump.

14. The cartridge assembly of claim 12, wherein the pump segment tubing comprises flexible tubing.

15. The cartridge assembly of claim 12, further comprising an upper semi- rigid tubing extending toward the upper end of the cartridge body, wherein the upper semi-rigid tubing is coupled to the upper tubing adapter.

16. The cartridge assembly of claim 12, further comprising a lower semi-rigid tubing extending toward the lower end of the cartridge body, wherein the lower semi-rigid tubing is coupled to the lower tubing adapter.

17. A method to install a removable tubing cartridge within an infusion pump, the method comprising:
- introducing an upper end of the cartridge to the infusion pump;
- engaging an upper lip of the cartridge with the infusion pump, wherein an upper tubing adapter cavity is formed in the upper lip, the upper tubing adapter cavity having a mating profile defining an opening of the upper tubing adapter cavity, wherein the mating profile defines a generally semi-circular mating profile extending from an edge of the upper lip, wherein the edge of the upper lip is configured to engage at least one upper pin of the infusion pump, and the semi-circular mating profile extends from the edge of the upper lip toward a cartridge body;
- frictionally engaging an upper tubing adapter within the mating profile via a spring bias of the upper lip;
- introducing a lower end of the cartridge to the infusion pump; and
- engaging at least one lower fastener of the cartridge with the infusion pump.

18. The method of claim 17, further comprising:
- inserting an upper tubing adapter into the opening of the upper tubing adapter cavity and engaging the upper tubing adapter with the upper tubing adapter cavity, wherein the upper tubing adapter is coupled to a first end of a pump segment tubing;
- engaging a lower tubing adapter to the cartridge, wherein the lower tubing adapter is coupled to a second end of the pump segment tubing; and
- longitudinally aligning the pump segment tubing relative to the cartridge.

* * * * *

UNITED STATES PATENT AND TRADEMARK OFFICE
CERTIFICATE OF CORRECTION

PATENT NO. : 11,141,527 B2
APPLICATION NO. : 16/175799
DATED : October 12, 2021
INVENTOR(S) : Brian William Ward et al.

It is certified that error appears in the above-identified patent and that said Letters Patent is hereby corrected as shown below:

In the Claims

Column 11; Line 54:
Replace "adapter is configured to engaged with the lower" with --adapter is configured to engage with the lower--.

Signed and Sealed this
Twenty-eighth Day of June, 2022

Katherine Kelly Vidal
*Director of the United States Patent and Trademark Office*